United States Patent [19]

Takada et al.

[11] Patent Number: 5,801,162
[45] Date of Patent: Sep. 1, 1998

[54] DERMATAN SULFATE COMPOSITIONS AND ANTITHROMBOTIC COMPOSITIONS CONTAINING SAME

[75] Inventors: Akikazu Takada, Hamamatsu; Junichi Onaya; Mikio Arai, both of Higashiyamato; Satoshi Miyauchi, Musashimurayama; Mamoru Kyogashima, Higashiyamato; Keiichi Yoshida, Higahimurayama, all of Japan

[73] Assignee: Seikagaku Kogyo Kabushiki Kaisha (Seikagaku Corporation), Japan

[21] Appl. No.: 446,662

[22] PCT Filed: Sep. 30, 1994

[86] PCT No.: PCT/JP94/01643

§ 371 Date: Aug. 28, 1995

§ 102(e) Date: Aug. 28, 1995

[87] PCT Pub. No.: WO95/09188

PCT Pub. Date: Apr. 6, 1995

[30] Foreign Application Priority Data

Sep. 30, 1993 [JP] Japan .................. 5-269758

[51] Int. Cl.$^6$ .................. A61K 31/715; C08B 37/00
[52] U.S. Cl. .................. 514/54; 536/53; 536/54; 536/55.1
[58] Field of Search .................. 536/53, 54, 55.1; 514/54

[56] References Cited

U.S. PATENT DOCUMENTS

| | | | |
|---|---|---|---|
| 4,783,447 | 11/1988 | DelBono et al. | 514/56 |
| 4,818,690 | 4/1989 | Paques | 435/13 |
| 4,943,630 | 7/1990 | Jacquinet et al. | 536/123 |
| 4,973,580 | 11/1990 | Mascellani et al. | 514/54 |
| 5,013,724 | 5/1991 | Petitou et al. | 514/54 |
| 5,116,963 | 5/1992 | Del Bono et al. | 536/21 |
| 5,118,793 | 6/1992 | Tollefsen et al. | 530/350 |
| 5,164,377 | 11/1992 | Van Dedem et al. | 514/54 |
| 5,252,339 | 10/1993 | Cristofori et al. | 424/479 |
| 5,382,570 | 1/1995 | Petitou et al. | 514/53 |
| 5,389,618 | 2/1995 | Debrie | 514/56 |

FOREIGN PATENT DOCUMENTS

| | | | |
|---|---|---|---|
| 0 238 994 | 9/1987 | European Pat. Off. | C08B 37/08 |
| WO 92/07954 | 5/1992 | WIPO | C12Q 1/56 |
| WO 93/05074 | 3/1993 | WIPO | C08B 37/00 |

OTHER PUBLICATIONS

CRC Handbook of Chemistry and Physics, 58th edition, R. C. Weist, editor, CRC Press, Inc., West Palm Beach, FL, 1978, pp. F124–F125.

Conrad *Ann. N.Y. Acad. Sci.* 1989, 556, 18–28.

K. Nagasawa et al., "The Structure of Rooster–Comb Dermatan Sulfate. Characterization and Quantitative Determination of Copolymeric, Isomeric Tetra–and Hexa–Saccharides" *Carbohydrate Research* 131:301–314 (1984).

M. Abbadini et al., "Dermatan Sulphate Induces Plasminogen Activator Release in the Perfused Rat Hindquarters" *Blood* 70(6):1858–1860 (1987).

A. Tripodi et al., "Effects of Subcutaneously Administered DermatanSulfate (MF 701) on the Coagulation and Fibrinolytic Parameters of Healthy Volunteers" *Thrombosis Research* 62:663–672 (1991).

J. Fareed et al., "An Overview of Non–Heparin Glycosaminoglycans as Antithrombotic Agents" *Recent Advances in Blood Coagulation* pp. 169–187, 1993.

*Primary Examiner*—Kathleen K. Fonda
*Attorney, Agent, or Firm*—Testa, Hurwitz & Thibeault, LLP

[57] ABSTRACT

Dermatan sulfate compositions having certain characteristics have been found to have thrombolytic activity. Dermatan sulfate combined with tissue plasminogen activator (t-PA) enhances the thrombolytic activity of t-PA. Antithrombotic compositions containing dermatan sulfates can be used for treating various thrombotic diseases.

19 Claims, 4 Drawing Sheets ic activity of dermatan sulfate administered in the living body composed of both anticoagulation and fibrinolytic activities is particularly significant for specific dermatan sulfates having intrinsic viscosity of 0.8 100 mL/g or over, specific detmatan sulfates derived from chicken crest, specific dermatan sulfates having a ΔDi-OS at a rate of 2–7% in their constructing disaccharide, or specific dermatan sulfates having average molecular weight of 25,000–100.000 dalton determined by the method described later, and additionally particular specific dermatan sulfates having very low content of heparin or heparan sulfate among dermatan sulfates aforementioned. The present invention is accomplished by the above mentioned findings.

DERMATAN SULFATE COMPOSITIONS AND ANTITHROMBOTIC COMPOSITIONS CONTAINING SAME

This is the U.S. national stage entry under 35 U.S.C. § 371 of PCT/JP94/01643, filed Sep. 30, 1994.

TECHNICAL FIELD

This invention relates to antithrombotic agents which prevent the extension of thrombi and stimulate lysis thereof.

BACKGROUND ART

Thrombosis is a disease caused by blood coagulation in living blood vessels due to the imbalance of platelets, coagulation and fibrinolytic system which basically should maintain fluidity of blood in the blood vessels. Thrombi in coronary arteries cause myocardial infarction and those in venous vessels in the lower limbs and so forth cause deep vein thrombosis. Abnormal activation of coagulation system due to severe infectious diseases or tumors leads to thrombi in systemic capillary blood vessels and results in disseminated intravascular coagulation syndrome (hereinafter referred to DIC). The DIC caused by severe infectious diseases often complicates by multiple organ failure and very poor prognosis. Various countermeasures have been developed to treat the thrombosis which shows extremely various symptoms depending on the sites of onset. Urokinase, tissue plasminogen activator (hereinafter referred to t-PA) or heparin and so forth have been used for the treatment of myocardial infarction and deep vein thrombosis and heparin has also been applied to DIC. However, urokinase has drawbacks of low affinity to fibrin, and t-PA is expensive and has very short half-life. In addition, percutaneous transluminal coronary recanalization and reperfusion therapy by direct peripheral intravenous administration with t-PA are liable to cause recurrence of thrombosis. Heparin has problems which requires at a definite concentration or over of antithrombinIII to secure the desired effect to exert its therapeutic effect. Furthermore, these drugs cause serious adverse effect of bleeding, thus synthetic antiprotease drugs have been developed to cope with the difficulties. However, no sufficient solution of the adverse effect has been obtained and problems such as an extremely short half-life remain unsolved.

Dermatan sulfates have been reported to exert anticoagulant activity via heparin cofactorII, but on their fibrinolytic activity, acceleration of release of t-PA by dermatan sulfates has been reported (Abbadini, M. et al., blood, 1987, 70, 1858–1860). while, no effect of dermatan sulfates on the amount of t-PA or fibrinolytic activity (Tripodi, A. el al., Thromb. res., 1991, 62, 663–672) has been reported and definite effect on fibrinolytic system is unclear.

Dermatan sulfates which have been used in various experiments or as a medicine under development are derived from intestine or skin of porcine or bovine (Pareed, J. et al., recent Advances in Blood Coagulation, 1993, 6, 169–187). No activity of dermatan sulfates derived from the other origins has been known.

DISCLOSURE OF INVENTION

The inventors of the present invention have been investigating the effect of dermatan sulfates on the fibrinolytic system and found that thrombolytic activity is enhanced by their presence in comparison to that in their absence. In addition, the inventors found that cumulated antithrombotic activity of dermatan sulfate administered in the living body composed of both anticoagulation and fibrinolytic activities is particularly significant for specific dermatan sulfates having intrinsic viscosity of 0.8 100 mL/g or over, specific detmatan sulfates derived from chicken crest, specific dermatan sulfates having a ΔDi-OS at a rate of 2–7% in their constructing disaccharide, or specific dermatan sulfates having average molecular weight of 25,000–100.000 dalton determined by the method described later, and additionally particular specific dermatan sulfates having very low content of heparin or heparan sulfate among dermatan sulfates aforementioned. The present invention is accomplished by the above mentioned findings.

The present invention relates to the antithrombotic containing the effective ingredient of dermatan sulfates shown above or to combined use of dermatan sulfates with tissue plasminogen activator (t-PA).

Dermatan sulfates have a main structure of repeating disaccharide composed of N-acetyl-D-galactosamine-4-sulfate and L-iduronic acid including a small amount of D-glucuronic acid and have different contents of sulfuric acid and D-glucuronic acid, and different binding sites of sulfuric acid and so forth, depending on the source of animal species and organs and so on.

Dermatan sulfates can be produced generally from raw materials of mammals and so forth such as bovine or porcine intestinal mucosa or skin, or chicken crest.

The present inventors found that the activation of plasminogen with single- or two-chain t-PA can be enhanced in the presence of dermatan sulfates obtained from these raw materials or their pharmacologically acceptable salts comparing to the case in the absence thereof. Furthermore, the present inventors also found that the specific dermatan sulfates of the present invention having intrinsic viscosity of 0.8 100 mL/g or over, preferably 9–2.0 100 mL/g, being derived from rooster comb, 2–7% of ΔDi-OS, preferably 3–6%, in their constructing disaccharide, and an average molecular weight of 25,000–100,000, preferable 30,000–60,000 dalton determined by gel filtration described later in Biochim. Biophys, Acta, 1117, 60–70 (1992), particularly those having very low content of heparin or heparan sulfate or pharmacologically acceptable salts thereof administered in the living body can be maintained for a longer duration in the blood than the other dermatan sulfates and exhibit pharmacological effect of all-embracing antithrombotic activity not only with fibrinolytic activity but also with anticoagulant activity and accomplished the present invention.

The pharmacologically acceptable salts of dermatan sulfates include such as sodium, potassium, lithium and calcium salts, but sodium salts are generally administered. The tissue plasminogen activators (t-PAs) used for the present invention include both endogenous and exogenous, single- and two-chain, and natural and gene recombinant products. Furthermore, t-PA analogies partially defective in amino acid composition or having extra amino acids may be used in so far as they exhibit plasminogen activating property (see EP-A-112122).

Dermatan sulfates or pharmacologically acceptable salts thereof (hereinafter may be referred to DS) sufficiently exhibit their pharmacological activity with single and sole or once or repetitive administration. The dermatan sulfates can be administered by intravenous, intraarterial or intracoronary arterial injections and may be used subcutaneously or intramuscularly. DS and t-PA can be administered simultaneously in the same routes or separately.

When the blood concentrations of DS and t-PA are expected to become excessive to the effective concentrations by aforementioned intracoronary arterial or intravenous administrations, then intramuscular or subcutaneous administration may be adopted other than the aforementioned routes.

Pharmaceutical preparations of dermatan sulfates can be suitably prepared with conventional pharmaceutically acceptable adjuvants such as stabilizers, emulsifiers, osmotic pressure moderators, pH adjusting agents and so forth.

DS is singly administered at doses of 50–3,000 mg/day in total for an adult patient and may be concurrently administered with 10,000–500,000 I.U. (international unit) of t-PA. These effective ingredients may be used once or dividedly in two to several portions in a day with suitable intervals. Furthermore, DS may be intravenously administered for consecutive several days.

As shown above, DS or pharmacologically acceptable salts thereof can be used to activate fibrinolytic activity as a useful thrombolytic accelerator. Particularly the specific DS of the present invention having characteristic features of intrinsic viscosity of 0.8–2.0 100 mL/g. derived from chicken crest, having ΔDi-OS at a rate of 2–7% in their constructing disaccharide, or having an average molecular weight of 25,000–100,000 dalton determined by the method described later, especially those having a very low content of heparin or heparan sulfate or pharmacologically acceptable salts thereof exhibit marked effects. While, those having intrinsic viscosity over 2.0 100 mL/g or average molecular weight of over 100,000 dalton show elevated viscosity in highly concentrated solutions and are not recommended because of disturbed blood flow rate. Furthermore, concurrent administration of DS described above or their pharmacologically acceptable salts and t-PA markedly increase the thrombolytic activity and can reduce the dose of t-PA for the treatment and prevention of thrombosis as useful thrombolytic agents.

Particularly, aforementioned specific DS or their pharmacologically acceptable salts of the present invention maintain effective blood concentration for a long duration than those of the other DS or their pharmacologically acceptable salts and exhibit prevention of expansion and inhibition of thrombogenesis, or stimulate the thrombolysis when administered in the living body. Thus, they provide excellent effects against disseminated intravascular coagulation (DIC) syndrome, multiple organ failure accompanied with multiple thrombi, and deep vein thrombosis, etc. These effects can be observed not only in the aforementioned diseases but also in all types of thrombi and used for their treatment and prevention in arteries, capillaries and veins. Furthermore, the specific DS or their pharmacologically acceptable salts of the present invention can be used for the prevention of blood clotting in the extracorporeal circulation such as haemodialysis for patients suffering from renal disease.

Heparin (hereinafter referred to Hep) or heparan sulfate (hereinafter referred to HS) contaminating in DS can be removed to give Hep or HS free DS (hereinafter referred to DS-H(−)). Intravascular, subcutaneous or intramuscular infection of the resultant DS-H(−) Provides decreased occurrence of adverse reactions such as bleeding. Especially, administration to patients with bleeding tendency due to decreased platelets and coagulation factors provides decreased occurrence of adverse reactions such as bleeding and is particularly safe.

BEST MODE FOR CARRYING OUT THE INVENTION

Figure 1:
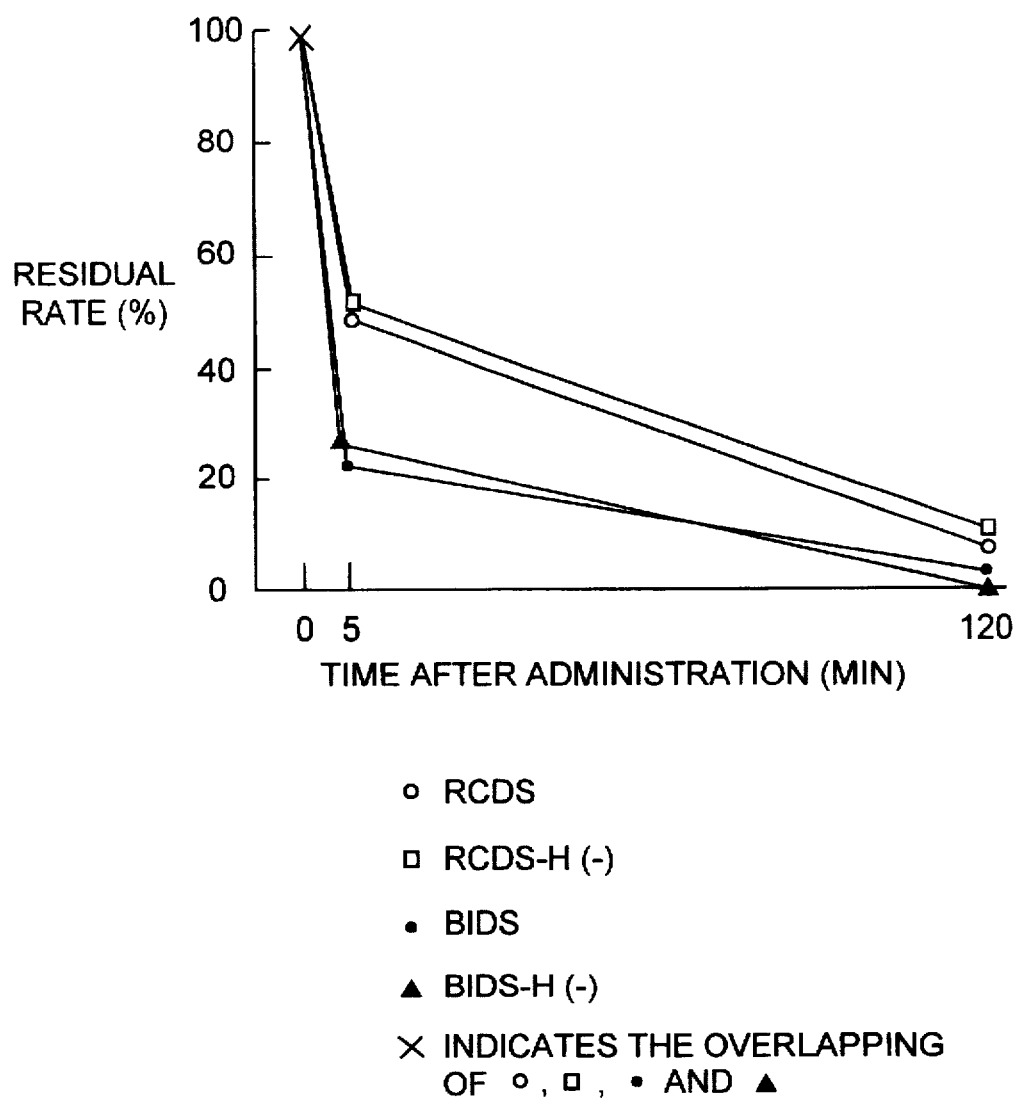
FIG. 1 shows the changes of blood concentration in rats of sodium dermatan sulfates derived from chicken crest (see Reference example 1, CCDS) and from bovine small intestine (see Reference example 2, BIDS) (see Example 1). ● shows administration of BIDS, ○ shows administration of CCDS, ▲ shows administration of BIDS-H(−), □ shows administration of CCDS-H(−) and X shows overlapping of ●, ○, ▲ and □.

The present invention will be practically explained by the following Reference examples and examples.

REFERENCE EXAMPLE 1

(1) Preparation of DS from hen crest

One kilogram of chicken crest was minced, boiled in hot water and digested at 50° C. for 12 hrs, with 5 g of Pronase (Kaken Pharmaceutical Co., Ltd., Trade name). The digested mixture was filtered through dialomaceous earth and the filtrate was adjusted pH 5.8–6.3 and digested at 50° C. for 3 hrs. with 1,000 TRU of a hysluronidase derived from Streptomyces microorganisms (Seikagaku Corp.). The digested mixture was added with NaCl up to 0.65M and poured onto an anion exchange resin column of 3×20 cm (Diaion$^{RTM}$ HPA-10, Mitsubishi Kasei Corp.) equilibrated with 0.5M NaCl solution. The column was successively washed with 0.5 L of 0.65M NaCl and 0.3 L of 1.1M NaCl solutions, then eluted with 1.8M NaCl solution. The eluted fractions were collected, evaporated under reduced pressure. The combined condensed fractions was dialyzed overnight against distilled water. The dialysate was evaporated to 10 mL and mixed with 5M NaOH to give 0.5M NaOH solution. The alkaline solution was kept at 37° C. for 90 minutes, cooled and neutralized with acetic acid glacial. The neutralized solution was fixed with 2-fold volume of ethanol. The formed precipitates were washed successively with 70% ethanol, pure ethanol and ether, and dried over phosphorous pentoxide under reduced pressure.

In 125 mL of water, 5 g of the dried precipitates were allowed to stand overnight and a small amount of undissolved precipitates were removed by centrifugation at 10° C. and 10,000 rpm for 15 minutes. The supernatant was diluted with 126 mL of 10% aqueous sodium acetatis solution, mixed wills ethanol in an ice bath to give final concentrating of 45%. and allowed to stand at 4° C. for 20 hrs. The centrifuged precipitates were successively washed with 90% ethanol, pure ethanol and ether, and dried over phosphorous pentoxide under reduced pressure to give pure DS sodium salt (hereinafter referred to CCDS).

The isolation and purification of dermatan sulfates from chicken crest can be performed not only by the method shown above but also by methods disclosed in Japanese Published Examined Patent Application Nos. 9042 (1985) and 21241 (1986).

(2) Removal of heparin (Hep) and heparan sulfate (HS) from DS

A small amount of Hep and HS contaminating DS can be removed by one of the following methods.

1) Ion exchange chromatography method

Fifty grams of CCDS obtained by the preceding method (1) wag planed on an anion exchange resin. Diaion$^{RTM}$ HPA11 (Mitsubishi Kasei Corp.) previously equilibrated with 1.1M NaCl, of column of 4.5×27 cm, washed with 8 L of 1.1M NaCl and eluted with 8 L of 1.5M NaCl solution. The pooled eluate was condensed with a rotary evaporator, dialyzed and precipitated by the addition of ethanol up to 42% or lyophilized to give standard CCDS (CCDS-H(−)) free from Hep and HS.

2) Nitrous acid cleavage method

The cleavage was performed by the method of Shively and Conrad (Biochemistry, 15, 3932–3942, 1976). That is, a mixture of 400 mL of 0.124 g/mL of barium nitrite monohydrate and 400 mL of 1N $H_2SO_4$ prepared at −10° C. was centrifuged at 3,000 rpm for 2 minutes to give 500 mL of a supernatant. To 500 mL of 0.1 mg/mL of CCDS, :500 mL of the supernatant was admixed and allowed to stand for 10 minutes at room temperature. The mixture was neutralized with $Na_2CO_3$ solution. The procedures after condensation were carried out as those in procedure 1) to give standard CCDS (CCDS-H(−)) free from Hep and HE.

REFERENCE EXAMPLE 2

Preparation of DS from Mucosa of Bovine Small Intestine

Ten kilograms of bovine small intestine was cut into pieces, followed by removal of feces and fats, then the mucosa was isolated. The mucosa was mixed with NaOH, adjusted to 3 L of 2.5N NaOH solution and extracted at 37° C. for 2 hrs. The extract was neutralized, filtered through diatomaceous earth, dialyzed and centrifuged to give a supernatant. The supernatant was mixed with an equal amount of ethanol and 5 g of sodium acetate to give precipitates. The collected precipitate was dissolved in 0.65M NaCl solution and afterward, in a similar manner with that of Reference example 1, poured onto an anion exchange resin column. The column was successively washed with 0.65M and 1.1M NaCl solutions and eluted with 1.5M NaCl solution. The combined eluate fraction was dialyzed against distilled water and the dialysate was admixed with calcium acetate and acetic acid to the final concentrations of 5% and 0.5M, respectively. Ethanol was added to the solution and the fraction precipitated at 15–30 v/v% were collected. The collected precipitate was converted to sodium salt thereof with an ion exchange resin, and flashed and dried in a similar manner with that of Reference example 1 to give DS sodium salt (hereinafter referred to BIDS).

Hep or HS was removed from BIDS in a similar manner with that of Reference example 1 (2) 2) to give BIDS-H(−).

Comparison of characteristic features of dermatan sulfates were carried out with dermatan sulfate derived from porcine intestinal mucosa (Celsus Lab. Inc. and distributed by Cosmobio Co. Ltd.) and that from porcine shin (SeiKagaKu Corp.).

REFERENCE EXAMPLE 3

Comparison of Physicochemical Properties of Various Dermatan Sulfates with Different Origins (1) Determination of average molecular weight The average molecular weight of DS was determined according to the method of Arai et al. (Biochim. Biophys. Acta, 1117, 60–70, 1992). That is, gel filtration with high performance liquid chromatography (HPLC) using glycosaminuglycans with the known molecular weight as a standard sample was applied and the molecular weight was determined from their relatively eluted fractions. A series of columns were prepared of TSKgelG4000PWX$_L$, G3000PX$_L$ and G2500PWX$_L$ (TOSOH Corp.) with 7.8 mm inner diameter and 300 mm length, respectively, eluted with 0.2M NaCl solution at a flow rate of 0.6 mL/minute, and detected with a differential refractometer.

(2) Analysis of composition of disaccharides

The determination of the site of sulfuric acid moiety of DS was performed according to New Biochemical Experiments 3, Saccharide II, DP. 49–62 (1991) (pub. by Tokyo Kagaku Dozin Co., Ltd.). That is, DS was digested with chondroitinase ABC and the produced disaccharide having unsaturated bond (unsaturated disaccharide) was analyzed with HPLC as it is and compared with that of the chondro-6-sulfatase treated aforementioned unsaturated disaccharide. The conditions of digestion with chondroitinase ABC, desulfation with chondro-6-sulfatase, and analysis with HPLC are shown below.

a) Digestion with chondroitinase ABC

According to Yoshida's procedure (Anal. Biochem., 77, 327–332 (1989)), in 20 µL of 10 mg/mL aqueous solution of DS, 20 µL of 0.4M Tris-HCl buffer (pH 8.0), 20 µL of 0.4M sodium acetate and 20 µL of 0.1% bovine serum albumin, and 120 µL of water were added, then 20 µL of 5 U/mL of chondroitinase ABC was added and incubated at 37° C. for 2 hrs.

b) Digestion with chondro-6 sulfatase

In 100 µL of the above mentioned chondroitinase ABC digested product, 20 µL of 5 U/mL chondro-6-sulfatase dissolved in 20 mM Tris-acelic acid buffer (pH 7.0) was added and incubated at 37° C. for 2 hrs.

c) Analysis with HPLC

Fifty microliters of the solution digested with chondroitinase ABC or further digested with chondro-6-sulfatase was analyzed with an HPLC apparatus (Hitachi Ltd.). An ion exchange column (YMC-Pack PA-120–S5, 2.6 mm in inner diameter and 250 mm in height) was used and the absorbancy aj 232 nm was determined. The elution was performed at a flow rate of 1.5 mL/minute with concentration gradient of 300 mM sodium hydrogenphosphate from 0% to 100% in 60 minutes. The peaks of eluted unsaturated disaccharides having sulfuric acid residue at various sites were identified.

(3) Determination of intrinsic viscosity

The determination of intrinsic viscosity was carried out according to Japanese Pharmacopoeia XII with an automatic viscometer (Rigosha Co., Ltd., VMC-052 type). A solution of 0.2M NaCl was used as a solvent and also used for the determination of flowing time in Ubbelohde viscometer. Determination of viscosity was performed at 30°±0.1° C. and three consecutive data of flowing time with differences within 0.1 sec. was used for the calculation of the intrinsic viscosity. The flowing time was rounded at 0.01 sec, and calculation of the values of intrinsic viscosity was carried out by the following equation.

$$\eta red = (t/t_0 - 1)/C$$

in which $t_s$=flowing rate of solution, $t_0$=flowing rate of solvent, and C=concentration of sample (w/w %) were used.

The reduced viscosity ($\eta red=(t_s/t_0-1)/C$ was plotted on a vertical axis against the concentration on a horizontal axis, and the Intrinsic viscosity was obtained from an intercept in the vertical axis by extrapolation of the obtained straight line to the concentration "0".

(4) Results

Table 1 summarizes the results of experiments (1)–(3). The average molecular weight of DS derived from chicken crest was 38,000 dalton with intrinsic viscosity of 1.21. In contrast, the other three DSs had quite different physico-chemical properties and showed average molecular weight of 14,000–16,000 with intrinsic viscosity of 0.44–0.68, indicating marked difference between DS derived from rooster comb and those derived from the other sources. The average molecular weight of DSs derived from bovine and porcine intestines was 16,000 and 18,500, respectively, by the method of the present inventors as shown in Table 1 though they had been reported as 25,000 (Thromb. Res., 71, 417–422, 1993) and 35,700 (Blood, 74, 1577–1582, 1989), respectively.

TABLE 1

Physicochemical properties of various dermatan sulfates

| Dermatan sulfate | Bovine intestine | Porcine intestine | Porcine skin | Chicken crest |
|---|---|---|---|---|
| Average molecular weight | 16,000 | 18,500 | 14,000 | 38,000 |
| Intrinsic viscosity (100 mL/g) | 0.68 | 0.58 | 0.44 | 1.21 |
| Composition of disaccharide (%) | | | | |
| ΔDi-0S | 0.60 | 0.69 | 0.34 | 4.97 |
| ΔDi-6S | 2.52 | 4.85 | 0.85 | 4.41 |
| ΔDi-4S | 87.22 | 83.83 | 90.22 | 82.91 |
| ΔDi-diS$_D$ | 0.16 | 0.61 | 0.22 | 0.92 |
| ΔDi-diS$_E$ | 7.65 | 6.31 | 8.38 | 6.13 |
| ΔDi-diS$_B$ | 1.58 | 3.59 | 0.00 | 0.65 |
| ΔDi-triS | 0.18 | 0.24 | 0.00 | 0.00 |

Abbreviations expressing the composition of disaccharide are shown in Table 2

TABLE 2

| | $R^1$ | $R^2$ | $R^3$ |
|---|---|---|---|
| ΔDi-0S | H | H | H |
| ΔDi-6S | $SO_3^-$ | H | H |
| ΔDi-4S | H | $SO_3^-$ | H |
| ΔDi-diS$_D$ | $SO_3^-$ | H | $SO_3^-$ |
| ΔDi-diS$_E$ | $SO_3^-$ | $SO_3^-$ | H |
| ΔDi-diS$_B$ | H | $SO_3^-$ | $SO_3^-$ |
| ΔDi-triS | $SO_3^-$ | $SO_3^-$ | $SO_3^-$ |

The present invention will be explained in detail by the following practical Reference example and Examples.

REFERENCE EXAMPLE 4

Determination of Hep or HS in DS

1) Method

Determination of Hep or HS in DS was performed by the following three methods.

a) Enzyme digesting method

Following three enzymes digest only Hep or HS but do not digest DS (New Biochemical Experiments, 3, SaccharideII, pp. 244–249, 1991, pub. by Tokyo Kagaku Dozin Co., Ltd.), thus, these properties are applied to the determinations. That Is, In 500 µg of DS obtained by Reference examples 1 or 2, three enzymes of 20 mU of heparitinase I, 20 mU of heparitinase II, and 50 mU of heparitinase IV dissolved in 10 µL of 20 mM Tris-HCl buffer, 10 mM $CaCl_2$ (pH 7.0) were added and incubated at 37° C. for 2 hrs. The reaction mixtures were analyzed by HPLC under the same conditions with those used for the determination of average molecular weight to detect and determine the formed unsaturated disaccharides with differential refractometer.

b) Determination of inhibitory activity of active type factor X with Hep or HS antithrombin W activation activity.

Hep or HS has an inhibitory activity against active type factor X (Xa) (hereinafter referred to anti-Xa activity), one of the coagulation factors, by activation of antithrombinIII, while DS has no such activity (Tolifsen, in "Heparin". pp. 257–273, Eds.; David A. Lane and Ulf Lindahl, Edward Arnold, London 1989). Applying this property, anti-Xa activity was determined using various concentrations of Hep to find a range having dose dependent relationship between the inhibitory activity and doses of Hep. The minimum dose of Hep for the maximum inhibition was found, wherein the inhibitory rate was regarded as 100%, and the inhibitory rate solely with antithrombinIII in the absence of Hep was regarded as 0%. The relationship was plotted to define a calibration curve. Similar determination was carried out for the DS samples of the present invention and the amount of Hep or DS was determined by comparing obtained anti-Xa activity to the calibration curve.

Practically, following procedure was carried out. 0.3 mL of 50 mM Tris-HCl (pH 8.0). 150 mM NaCl, 10 mM $CaCl_2$, (buffer), 0.1 mL of 1 U/mL of antithrombinIII (bovine, Sigma) and 0.1 mL of Hep (0.03–2 µg/mL, bovine intestine, Syntex) or 0.1 mL of DS samples (50–100 µg/mL) prepared as Hep or HS free as described before were mixed at 4° C. and then the mixture was incubated at 37° C. for 2 minutes. Next, 0.1 mL of Xa (7.1 nkat/mL. bovine. Chromogenic AB Co., Ltd., distributor Seikagaku Corp.) was added to the mixture and the mixture was incubated at 37° C. After 5 minutes, 0.1 mL of 100 µM of a synthetic substrate (Boc-Ile-Glu-Gly-Arg-MCA, code 3094V, Peptide Research Inst.) was added to the mixture to incubate at 37° C. for 3 minutes and the reaction was terminated by the adding 0.3 mL of 30% acetic acid. Finally, 1 mL of a solution comprising 7 volume of 50 mM of the aforementioned buffer and 3 volume of 30% acetic acid was added to the mixture to give the sample for determination. The determination war performed with a fluorophotometer (Japan Spectroscopic Co., Ltd., FP-777) al. excitation wave length of 350 nm and fluorescence wave length of 444 nm.

It was confirmed beforehand that anti-Xa activity of antithrombinIII itself was almost negligible in the absence of Hep or HS under the present determination conditions. The inhibitory rate was calculated by the following equation:

$$\text{Inhibitory rate} = 100 - \frac{A-B}{C-B} \times 100 (\%)$$

A ; determined value of sample containing Hep or DS.

B ; value obtained in the presence of a buffer instead of antithrombinIII, Hep or DS, and Xa in the above mentioned procedure.

C ; value obtained in the presence of a buffer instead of antithrombinIII In the above mentioned procedure.

c) Determination of inhibitory activity for active type factor II by Hep or HS through antithrombinIII activation action.

Hep or HS has an inhibitory activity against active type of coagulation factor II (IIa), one of tile coagulation factors, by activation of antithrombinIII, that is, antithrombin action (hereinafter referred to anti-Xa action). While Ds has no such activity (Tollfsen, In "Heparin". pp.257–273, Eds: David A. Lane and Ulf Lindahl, Edward Arnold, London 1989). Anti-IIa activity was determined with various concentration of Hep using the above mentioned property to define the dose dependent relationship range between the inhibitory activity and doses of Hep. The minimum dose of Hep for the maximum inhibition was found. wherein the inhibitory rate was regarded as 100% and the inhibitory rate solely with anti-thrombinIII in the absence of Hep was regarded as 0%. The relationship was plotted to define a calibration curve. Similar determination was carried out for the DS sample of the present invention and the amount of Hep or HS was determined by comparing obtained anti-Xa activity to the calibration curve.

Practically, following procedure was carried out. 0.35 mL of 20 mM Tris-HCl (pH 7.4), 150 mM NaCl, 10 mM $CaCl_2$, 0.1% bovine serum albumin (buffer) and 0.1 mL of anti-thrombin M (1 U/mL, bovine, Sigma), and Hep (0.3–20 µg/mL, bovine intestine, Syntex) or DS (50–100 µg/mL) prepared as Hep or HS free as described before were mixed at 4° C. and then the mixture was incubated at 37° C. for 2 minutes. Next, 0.05 mL of IIa (50 mU/mL bovine, Boehringer) was added to the mixture and the mixture was incubated at 37° C. After 5 minutes, 0.1 mL of 70 µM of a synthetic substrate of Bor-Val-Pro-Arg-MCA (code 3093V, Peptide Research Inst.) was added to the mixture and incubated at 37° C. for 3 minutes. The reaction was terminated by adding 0.3 mL of 30% acetic acid to the mixture. Finally, 1 mL of a solution comprising 7 volume of aforementioned buffer and 3 volume of 30%, acetic acid glacial was added to the mixture to give the sample for determination. The determination was performed with a fluorophotometer (Japan Spectroscopic Co., Ltd., FP-777) at excitation wave length of 350 nm and fluorescence wave length of 444 nm. It was confirmed beforehand that anti-IIa activity of antithrombin III itself was almost negligible in the absence of Hep or HS under the present determination conditions. The inhibitory rate was calculated by the following equation:

$$\text{Inhibitory rate} = 100 - \frac{A-B}{C-B} \times 100 (\%)$$

A ; determined value of sample containing Hep or DS.

B ; value obtained in the presence of a buffer instead of antithrombinIII, Hep or DS, and IIa in the above mentioned procedure. p1 C ; value obtained in the presence of a buffer instead of antithrombinIII in the above mentioned procedure.

2) Results

The results obtained by the above mentioned three methods are shown in Table 3.

TABLE 3

|            | method a) | method b) | method c) |
|------------|-----------|-----------|-----------|
| BIDS-H(−)  | 0.00%     | 0.013%    | 0.000%    |
| CCDS-H(−)* | 0.00%     | 0.023%    | 0.003%    |
| BIDS       | 0.81%     | 0.30%     | ND        |
| CCDS       | 0.26%     | 0.16%     | ND        |

ND: Not determined
*Sample free from Hep or HS prepared by the ion exchange chromatography mentioned in Reference example 1 (2) 1).

EXAMPLE 1

Differences in the Duration of Blood Concentration of CCDS, BIDS, CCDS-H(−) and BIDS-H(−) after Administration were Investigated in Rats (1) Materials and method 6.5–7.5 Week old of male Sprague-Dawley (SD) rats (Charles River Japan, Inc.) were used. CCDS, BIDS, CCDS-H (−) and BIDS-H(−) were used as test samples. Rats were anesthetized with ether and 10 mg/kg of each test sample was administered in tail vein. Blood was drawn from the inferior vena cava 5 and 120 minutes after the administration under ether anesthesia into tubes containing 1 volume of 3.2% citric acid per 9 volumes of blood. The plasma was isolated with centrifugation and the quantity of DS In plasma was determined according to "New Biochemical Experiments", 3, SaccharidesIII, pp. 175–179. That is, the plasma was desalted through a PD-10$^{RTM}$ column (Pharmacia Biochemicals Inc.), lyophilized, digested with chondroitinase ABC, ultrafiltered through a membrane with a cutoff molecular weight of 5.000 and the resultant filtrate was analyzed by HPLC.

(2) Results

The results are expressed in relative residual rate (%) of DS to that at time 0 (zero) and shown in FIG. 1. The residual rates of CCDS and CCDS-H(−) were about 2-times higher than those of BIDS and BIDS-H(−) at 5 minutes after the administration. CCDS and CCDS-H(−) showed about 10% residual rates at 120 minutes after the administration, while BIDS was scarcely detected. CCDS-H(−) showed slightly higher residual rate than that of CCDS at 5 and 120 minutes after the administration.

EXAMPLE 2

The Antithrombotic Effect of DS was Investigated in Rat Inferior Vena Cava Thrombosis Model.

(1) Materials 6.5–7.5 Week old male Sprague-Dawley (SD) rats (Charles River Japan, Inc.) were used. CCDS and BIDS were used as DS.

(2) Method

Preparation of experimental thrombosis model

Rat thrombosis model was prepared according to the method of Reyers et al. [Thromb. Res., 18, 669–674 (1980)]. That is, rats were laparotomized under anesthesia with Nembutal$^{RTM}$ (Dynabott-Dainippon Pharmaceutical Co., Ltd.) and ligated just below the branch of left renal vein of inferior vena cava with a surgical silk thread (No. 7. diameters of 0.48–0.56 mm: Shin-ei Co. Ltd.). The test samples of CCDS and BIDS were administered in the tail vein at doses of 1, 3 and 10 mg/kg at 1 minute prior to the ligation. Control group was given saline solution. Rats were laparotomized under ether anesthesia 3 hrs. after the ligation and the vein was incised to extirpate thrombi. The thrombi were allowed to stand overnight at 37° C. and the dry weight thereof was measured. The obtained data were statistically analyzed with Newman-Keuls method.

(3) Results

The results are shown in Table 3. The relative dry weight of thrombi of both DS groups administered 1 mg/kg to that of the control group showed 60% of inhibition rate. However, the weight of the thrombi of CCDS group decreased up to 2.4% and 0.0% at doses of 3 and 10 mg/kg or over, respectively, compared to that of the control group, while that of BIDS group decreased up to only 34.1% and 2.4% in comparison to that of the control group, respectively, indicating the usefulness of CCDS.

TABLE 3

Antithrombotic test in a rat inferior vena cava thrombosis model

| Test sample | Dose (mg/kg) | Average dry weight of thrombi (mg) | Relative weight ratio (%) |
|---|---|---|---|
| Saline (control) | — | 4.1 ± 0.7 | 100 |
| CCDS | 1 | 2.5 ± 0.9 | 61.0 |
|  | 3 | 0.1 ± 0.1** | 2.4 |
|  | 10 | 0.0 ± 0.0** | 0.0 |
| BIDS | 1 | 2.6 ± 0.6 | 63.4 |
|  | 3 | 1.4 ± 0.8* | 34.1 |
|  | 10 | 0.1 ± 0.1** | 2.4 |

*$p < 0.05$, **$p < 0.01$, compared to the control group.

Control group had 14 rats and two DS groups had 6 rats, respectively, and their mean values were calculated. cl

EXAMPLE 3

The Effects of DS on the Thrombogenesis and Thrombolysis were Investigated in a Thrombosis Model of Rat Inferior Vena Cava.

(1) Materials 6.5–7.7 Week old male Sprague-Dawley (SD) rats (Charles River Japan, Inc.) were used. CCDS and BIDS were used as DS.

(2) Method 1) preparation of experimental thrombosis model

Rat thrombosis model was prepared by ligation of the inferior vena cava in a similar manner to that of Example 2. The test samples were administered in the tail vein at doses of 3, 10 and 30 mg/kg, respectively, in 0.8 mL/kg. Control group was given saline solution. In the control group, 6 hrs. after ligation and in the test group, 2 hrs. after the administration (8 hrs. after ligation), rats were laparotomized under ether anesthesia and blood was drawn. Then, the veins are incised, thrombi were extirpated and allowed to stand at 37° C. overnight to determine the dry weight thereof. The resultant data were statistically analyzed by Newman-Keuls method.

2) Preparation of euglobulin fraction

In a plastic test tube, 0.5 mL of plasma was placed and 9.5 mL of deeply cooled 0.01N acetate buffer (pH 4.85) was admixed thereto, which was allowed to stand in a refrigerator for 1 hr., centrifuged at 3,000 rpm for 5 minutes to give an euglobulin fraction. The precipitates were admixed with 0.5 mL of Tris-HCl buffer (pH 7.4) to give a clear solution.

3) Determination of fibrinolytic activity

In a hole of fibrin test plate, 10 µL of euglobulin fraction was placed and left at 37° C. in an incubator for 18 hrs. and fibrinolytic area (square of diameter) was measured. The fibrinolytic area is proportional to the strength of plasmin activity. The resultant fibrinolytic data were statistically analyzed by Newman-Keuls method.

(3) Results

The results are shown in Table 4.

In the Table 4, Control-6 hrs. represents the group with laparotomy under anesthesia 6 hrs. after ligation of vein, followed by drawing blood and extirpating of thrombi. Control-8 hrs. represents the group with administration of saline solution 6 hrs. after ligation of vein, followed by drawing blood and extirpating thrombi after further 2 hrs.

1) Effects on inhibition of thrombogenesis and on thrombolysis.

Thrombi were observed in all groups, but marked differences were found among the groups as shown in Table 4. Both CCDS and BIDS administration groups showed dose dependent decrease in thrombi weight compared to that in Control-8 hrs. group. Furthermore, groups administered 30 mg/kg of BIDS and 10 mg/kg or over of CCDS exhibited lighter thrombi weight than that in Control-6 hrs. group indicating not only inhibition of thrombogenesis but also thrombolytic effect. In other words, CCDS showed more potent inhibitory effect on thrombogenesis and thrombolytic effect at smaller doses than that in BIDS group.

2) Effect on fibrinolytic system

CCDS and BIDS were administered at doses of 3, 10 and 30 mg/kg, respectively, and plasmin activity in plasma was determined after 2 hrs. (8 hrs. after ligation of vein). The results are shown in Table 4. Plasmin activity in CCDS group given 10 mg/kg and in BIDS group given 30 mg/kg or over was significantly higher than that in the control group. This results indicate the excellent effect of CCDS.

TABLE 4

| Test sample | Dose (mg/kg) | Dry weight of thrombi (% ratio to Control-8 hrs.) | Fibrinolytic activity FA[1] (% ratio to Control-8 hrs.) |
|---|---|---|---|
| Control-6 hrs. | — | 70 ± 9 | Not determined |
| Control-8 hrs. | — | 100 ± 11 | 100 ± 4 |
| CCDS | 3 | 73 ± 9 | 110 ± 5 |
|  | 10 | 56 ± 12 | 105 ± 10++ |
|  | 30 | 54 ± 11 | 204 ± 15++ |
| BIDS | 3 | 90 ± 18 | 108 ± 6 |
|  | 10 | 79 ± 10 | 114 ± 5 |
|  | 30 | 60 ± 8 | 158 ± 6++ |

[1])Area for fibrinolysis compared to Control-8 hrs.
++$p < 0.01$

Weight of thrombi was expressed as % ratio to Control-8 hrs. which was made 100%. Control-8 hrs. group had 16 rats and the other groups had 8–9 rats, respectively, and their mean values were calculated.

EXAMPLE 4

The Comparative Test of Antithrombotic Effects of DS on Endotoxin Induced Rat DIC Model (1) Materials 5.5–6.5 Week old male Sprague-Dawley (SD) rats (Charles River Japan, Inc.) were used. Rat was anesthetized with intraperitoneal injection of Nembutal[RTM] and the left thigh was incised. A polyethylene cannula (PE-10, Imamura Co. Ltd.) was retrogradingly inserted from the incised site to ventral vein at 4 cm distance therefrom and fixed after emergence, an endotoxin (*Escherichia coli* 055:B5, Difco Co., Ltd.) was continuously infused with an infusion pump (Model-22M, HARVARD) through a syringe at a rate of 3.75 mg/kg/hr. for 4 hrs. Test sample, CCDS-H(−) or BIDS-H(−), was simultaneously with endotoxin and continuously infused for 4 hrs. with a cannula attached to right vein. Control group was given equivalent volume of saline solution with that of test sample administered group for 4 hrs.

(2) Test items

After the administration of endotoxin, blood was drawn and kidneys were extirpated and the following items were determined.

1) Platelet count: Platelet was counted with an automatic hemacytometer (Celltac MEK-4500: Nippon Denko Co., Ltd.).

2) Fibrinogen: Plasma was isolated and determined with fibrinogen determination kit (Sunassay Fibrinogen$^{RTM}$, produced by NITTO BOSEKI Co., Ltd., distributed by SanKo Junyaku Co., Ltd.).

3) Fibrinogen-fibrin degradation products (FDP); Serum was isolated and FDP was determined with FDP determination latex reagent (FPDL$^{RTM}$ test, Teikoku Hormone Mfg. Co., Ltd.)

4) Renal glomerular fibrin deposit rate (%GFD): The kidneys were fixed with 10% neutral formalin buffer solution, embedded in paraffin, sliced and stained with phosphlolungslic acid-hematoxylin. Renal glomerular were microscopically observed in the whole field of the kidney specimens and the numbers of fibrin deposit were counted and expressed as percent ratio. The resultant data were statistically analyzed by Newman-Keuls method.

(3) Results

The results are shown in Table 5. Platelet count, fibrinogen and FDP was $75\times10^4$ µL, 216 mg/dL, and 2.5 µg/mL or less, respectively, and no %GFD was detected in normal group. However, endotoxin induced DIC rats showed abnormal corresponding rate of $14\times10^4$ µL, 35 mg/dL, 34.3 µg/mL and 61%, respectively.

DS-H(−) administered group showed improvement in all these parameters, and CCDS-H(−) group showed better results than those of BIDS-II(−) in all parameters. Particularly %GFD which is a cause of renal failure remained 16.1% in BIDS-H(−), while CCDS-H(−) group showed marked improvement with the decline to 1%, indicating usefulness of CCDS-II(−).

TABLE 5

Comparative test of antithrombotic effect of DS in endotoxin induced rat DIC model

| | Dose (mg/kg/ hr.) | Platelet ($\times 10^4$ µL) | Fibrinogen (mg/dL) | FDP (µg/mL) | % GFD |
|---|---|---|---|---|---|
| Normal | | 75 ± 1 | 216 ± 5 | <2.5 | 0.0 |
| Control (only LPS*) | | 14 ± 1 | 35 ± 3 | 34.3 ± 2.5 | 60.7 ± 5.3 |
| CCDS-H(−) + LPS | 5.0 | 22 ± 3 | 120 ± 6* | 4.6 ± 0.4* | 1.2 ± 0.7* |
| BIDS-H(−) + LPS | 5.0 | 18 ± 3 | 107 ± 10* | 8.6 ± 2.6* | 16.1 ± 5.5* |

(*endotoxin, *compared to control, p > 0.01)

The experiment was carried out in 19 rats for normal group, 20 rats for control group and 7 each rats for DS administration groups, and their average values were calculated.

EXAMPLE 5

Stimulative Effect of DS on Activation of Glu-plasminogen (Natural Plasminogen, Hereinafter Referred to Plasminogen) with t-PA (1) Method Fifty microliters each of various concentration of DS (BIDS, CCDS) or chondroitin sulfate (control group), 25 µL of 1.6 µM plasminogen and 25 µL of 20 nM of single or two-chain t-PA, and 100 µL of 0.6 mM a synthetic substrate S-2251 (H-D-Val-L-Leu-L-Lys-p-nitroanilide-2HCl) were mixed and the absorbancy at 405 nm was determined every 2 minutes with an automatic microtiter plate reader. The reaction was carried out at 37° C. in a buffer composed of 60 mM TriS-HCl with Tween$^{RTM}$ 80.

The initial rate of activation of plasminogen was calculated as follows; the slope of plots of, $A_{405}$, an absorbancy at 405 nm at time t to the square of time ($\Delta A_{405}/\Delta t^2$) was divided by 40,000 (Chibber, B. A. K., et al., Biochemistry, 1985, pp. 3429–3434). The stimulation rate was calculated from ratios to DS or chondroitin sulfate free conditions which was made the initial rate 1 (one).

(2) Results

Figure 2:
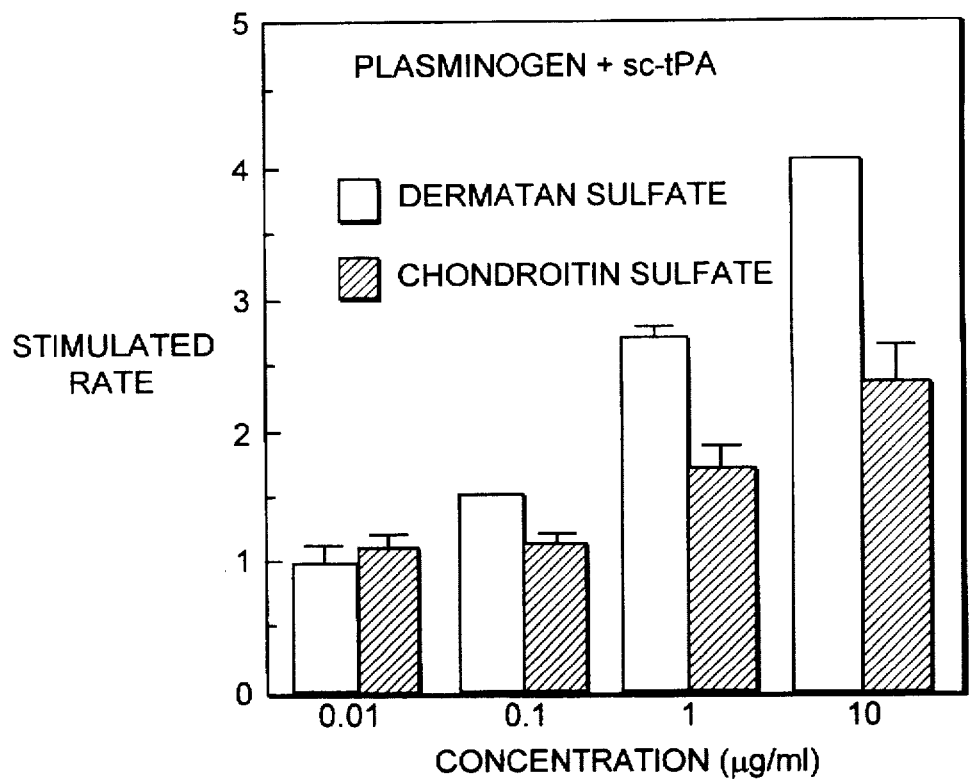
FIG. 2 shows the stimulative rate of BIDS on the activation of plasminogen with single-chain tissue plasminogen activator (sc-tPA).
Figure 3:
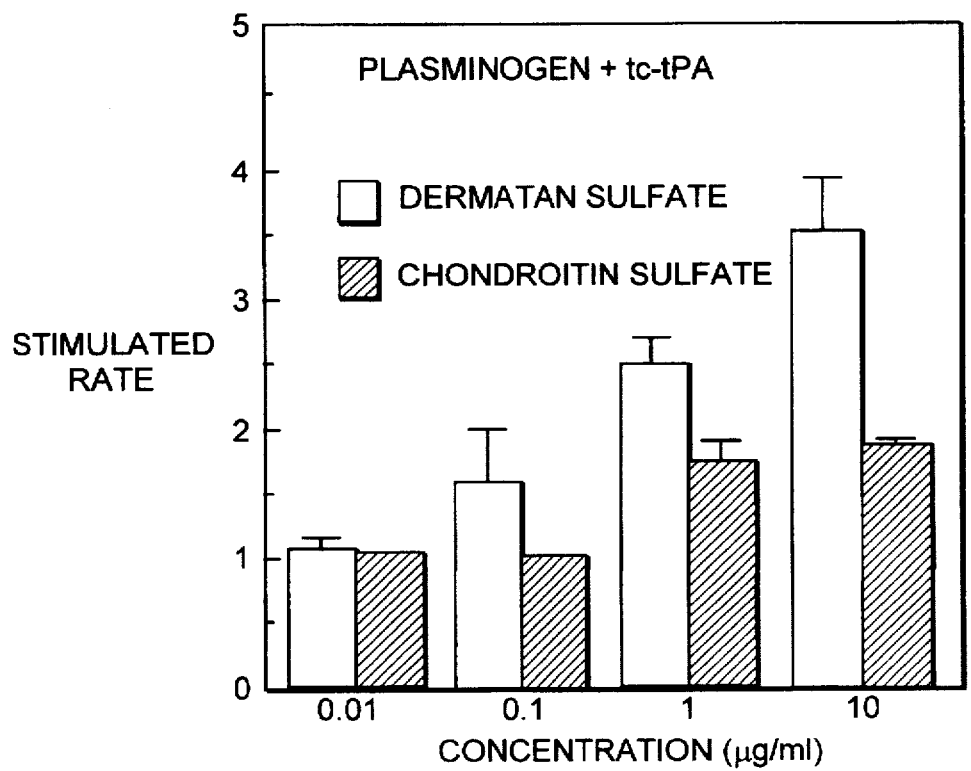
FIG. 3 shows the stimulative rate of BIDS on the activation of plasminogen with two-chain tissue plasminogen activator (tc-tPA).
Figure 4:
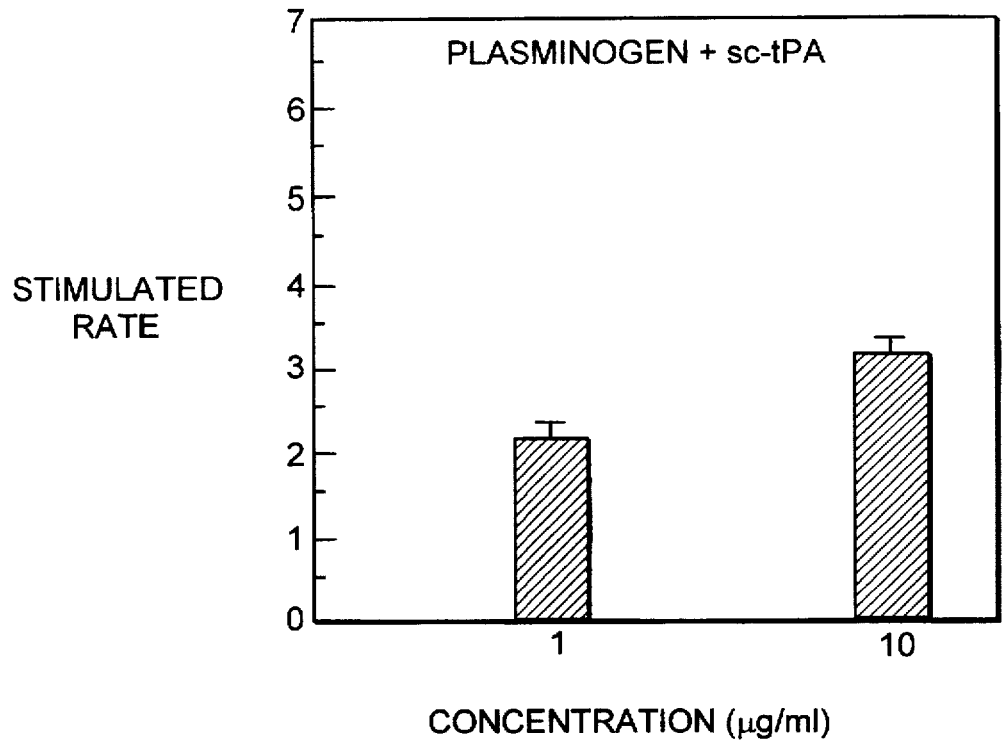
FIG. 4 shows the stimulative rate of CCDS on plasminogen activation with sc-tPA.
Figure 5:
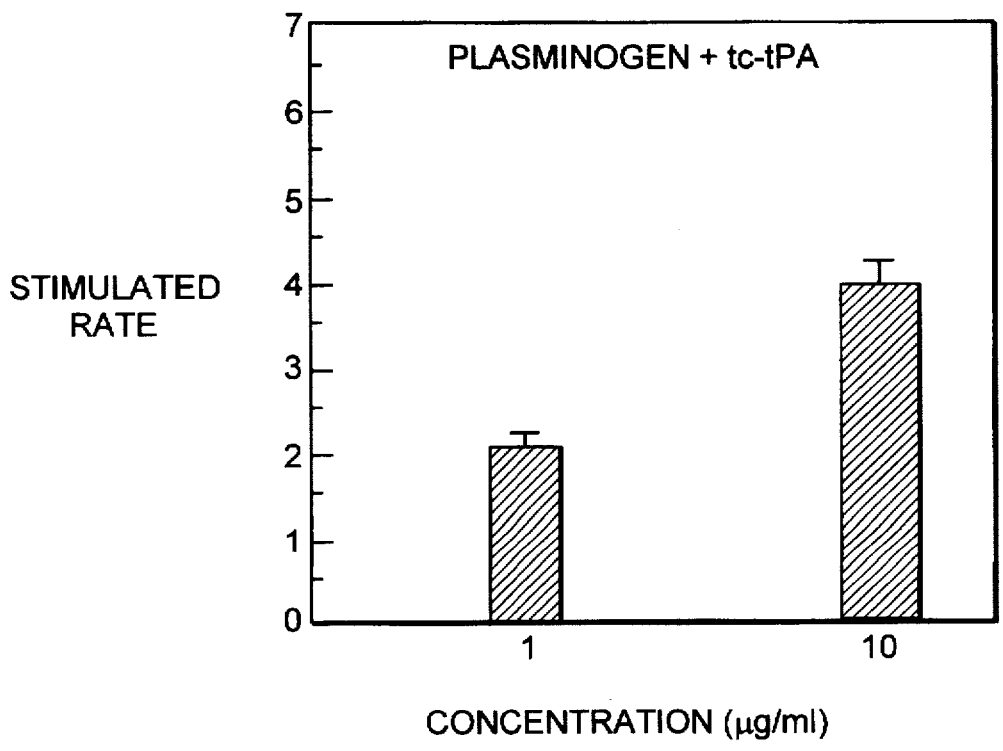
FIG. 5 shows the stimulative rate of CCDS on plasminogen activation with tc-tPA.

The results on BIDS are shown in FIGS. 2 and 3. DS dose-dependently stimulated the activation of plasminogen at 1.5- to 4.5-fold in the case of single-chain t PA (sc-tPA) and 1.5- to 3.5-fold in the case of two-chain t-PA (tc-tPA) as shown in these Figures. While, control group, chondroitin sulfate, showed weaker stimulation rates of maximum 2.5-fold in the presence of single-chain t-PA and maximum 1.5-fold In the presence of two-chain t-PA compared to those in DS group. The results on CCDS are shown in FIGS. 4 and 5. The CCDS also stimulated the activation of plasminogen at 2.0- to 4.5-fold in the presence of single chain t-PA (sc-tPA) and 2.0- to 4.0-fold in the presence of two-chain t-PA (tc-tPA), respectively.

EXAMPLE 6

(1) Materials and method

The effect of DS on rat fibrinolytic system was investigated.

9–11 Week old male Wistar rats were anesthetized with Somnopentyl$^{RTM}$ (Kyoritau Shoji Co., Ltd.) and 40 mg/kg of DS (BIDS) was subcutaneously administered on the back thereof. After 1, 6, 12 and 24 hrs., blood uas drawn with a syringe containing citric acid. Euglobulin fraction was prepared from plasma by a similar manner with that in Example 3 and fibrinolytic activity was evaluated by the fibrin plate method. The obtained data were statistically analyzed by Newman-Kleus method.

The amount of DS in plasma and euglobulin fraction was determined ("New Biochemical Experiments", 3, Saccharides II, pp. 175–179). Saline solution was used in the control group. These experiments were performed at a predetermined time in consideration of circadian rhythm of rat coagulative and fibrinolytic activities.

(2) Results

The obtained results are shown in Tables 6 and 7.

DS showed fibrinolytic activity up to 12 hrs. after the administration as shown in Table 6. About 70–80% of DS in plasma existed in euglobulin fraction and exhibited the fibrinolytic activity as shown in Table 7. CCDS also gave similar results.

TABLE 6

Fibrinolytic activity by fibrin plate method[1]

| Test sample | Time after administration (hrs.) | | |
|---|---|---|---|
| | 6 | 12 | 24 |
| Control | 57.4 ± 3.6 | 54.1 ± 3.9 | 42.3 ± 4.6 |
| DS | 85.3 ± 8.4* | 71.9 ± 3.5 | 46.1 ± 3.7 |

[1])Fibrin dissolution area (mm$^2$)
*p < 0.01 to the control

Both control and DS groups had 4–5 rats and the mean values were calculated.

TABLE 7

DS in plasma and euglobulin fraction (μg/mL)

| Fraction | Time after administration (hrs.) | | | |
|---|---|---|---|---|
| | 1 | 6 | 12 | 24 |
| Plasma | 3.62 ± 0.61 | 3.58 ± 0.27 | 2.20 ± 0.26 | 0.47 ± 0.04 |
| Euglobulin | 2.51 ± 0.62 | 2.80 ± 0.27 | 1.60 ± 0.16 | N.D. |
| Control | 0.03 ± 0.02 | | | |

N.D.: Not determined

Both control and DS groups had 4–5 rats and the mean values were calculated.

EXAMPLE 7

Stimulative Effect of DS on Lysis of Human Plasma Clot was Investigated.

(1) Method

In 96 wells microtiter plate, 40 μL each of various concentrations of DS (BIDS) (final concentration of 50.0–200 μg/mL). 20 μL of single-chain t-PA (final concentration of 166.7 U) 40 μL of thrombin (final concentration of 20 U/mL) and 100 μL of human plasma were placed and mixed. The absorbancy at 340 nm was determined immediately after the preparation and then every 10 minutes to give the minimum absorbancy (Min.). The fibrinolytic activity is expressed by using a ratio of DS-PLT1/2 (minutes), obtained by division by 2 of the sum of maximum absorbancy (Max.) and Min. in the presence of DS to Cont-PLT1/2 of the control group.

(2) Results

Figure 6:
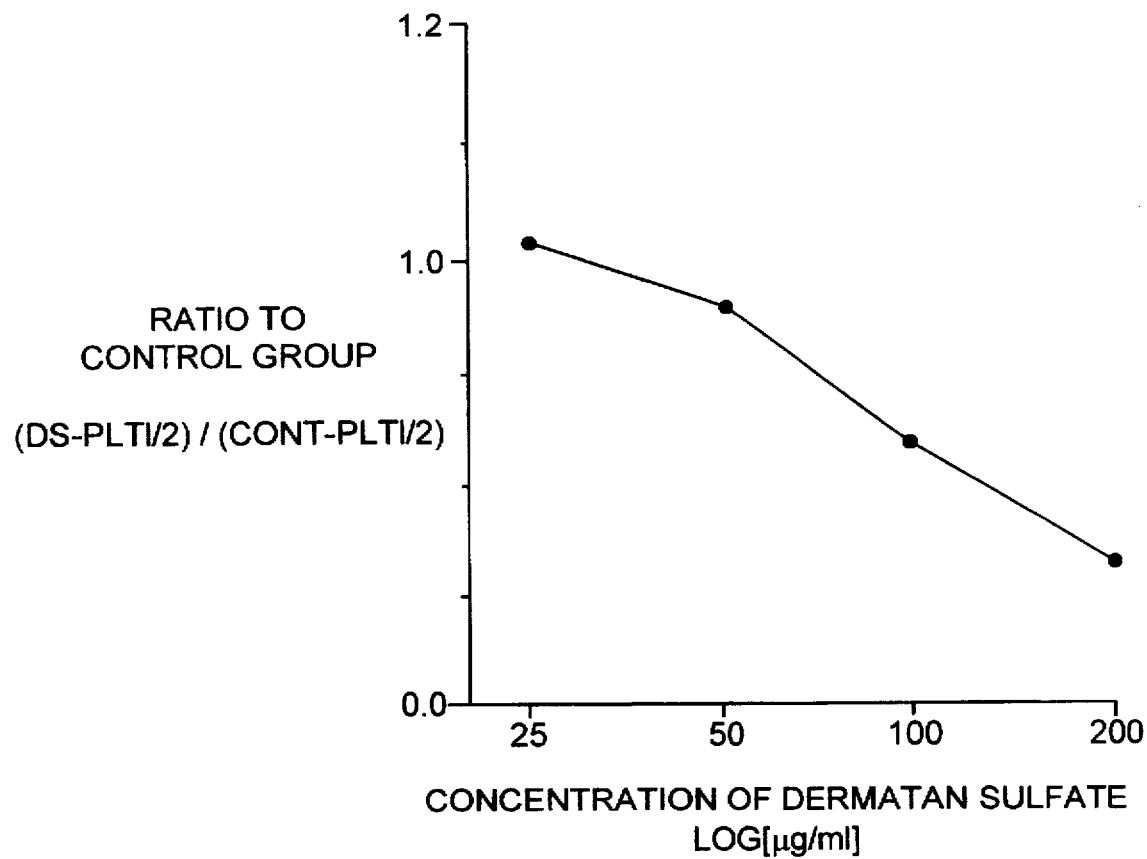
FIG. 6 shows the stimulative effect of lysis of BIDS on human plasma clot.

The results are shown in Table 6. DS dose-dependently stimulated the fibrinolytic activity of plasma clot as shown in FIG. 6. CCDS gave similar results.

EXAMPLE 8

Toxicity Test of Dermatan Sulfate with Single Intravenous Administration in Mice.

(1) Materials and method

Five week old Crj;CD-1 mice of both sexes (Charles River Japan, Inc.) were used. Isotonic solutions of CCDS-H(−) and BIDS-H(−) were prepared with sterile distilled water and sterile saline solution and 2,000 mg/kg was intravenously administered, respectively, once in the mouse tail vein with a glass syringe. The animals had been observed for the appearance of signs of toxicity for 14 days.

(2) Results

Neither DS groups showed death even at a high dose of 2,000 mg/kg as shown in Table 8. The lethal dose under the present test conditions is presumed to be over 2,000 mg/kg.

TABLE 8

| Test sample | Dose (mg/kg) | Number of death/number of used mice | |
|---|---|---|---|
| | | Male | Female |
| CCDS-H(−) | 2,000 | 0/5 | 0/5 |
| BIDS-H(−) | 2,000 | 0/5 | 0/5 |

EXAMPLE 9

Pharmaceutical Preparation (1) In sterile saline solution or sterile distilled water. 500–5,000 mg of sterilized sodium salt of DS [CCDS or CCDS-H(−)] derived from chicken crest obtained by Reference example 1 was dissolved to give isotonic solutions and adjusted to 100 mL. The solution was poured 10 mL each in ampoules to give intravascular, subcutaneous or intramuscular injection preparations.

(2) Two hundred and fifty milligrams of sodium salt of DS [CCDS or CCDS-II(−)] obtained from chicken crest by Reference example 1, and 1,00,000 IU of t-PA were separately packaged to give injection preparations which are dissolved in the solution just before use. The injection preparations are used for intra-coronary artery or intravenous injection.

Industrial Applicability

Dermatan sulfates or pharmacologically acceptable salts thereof stimulate the fibrinolytic activity and can be used for thrombolytic stimulator.

In addition, combined use of dermatan sulfates including sodium salts thereof with tissue plasminogen activators (t-PA) markedly increase the thrombolytic action and can decrease the dose of t-PA.

Furthermore, the particular dermatan sulfate of the present invention, that is, dermatan sulfate having intrinsic viscosity of 0.8 100 mL/g or over, derived from chicken crest, having 2–7% of ΔDi-OS in their constructing disaccharide, having average molecular weight of 25,000–100,000 dalton determined by the gel filtration method according to Biochim. Biophys. Acta, 1117, 60–70 (1992), or above mentioned specific dermatan sulfates containing very little amount of heparin or heparan sulfates or their pharmacologically acceptable salts maintain effective blood concentration thereof for a long duration and prevent expansion of thrombosis, inhibit thrombogenesis and so forth.

Therefore, the antithrombotic agents of the present invention are useful for the treatment and prevention of myocardial infarction, disseminated intravascular coagulation (DIC) syndrome, multiorgan failure accompanied with multiple thrombosis, deep vein thrombosis and so forth. Furthermore, the agents can be indicated for the prevention of blood coagulation during extracorporeal circulation such as haemodialysis for patients suffering from renal disease, etc. Furthermore, DS has less adverse effect such as bleeding, etc, compared to that of Hep. DS-H(−) obtained by removal of Hep and HS from DS provides improved safety together with far less adverse reaction such as bleeding, etc. Thus, the resultant product preferably can be indicated for patients with bleeding tendency or compromised platelets and coagulation factors.

We claim:

1. Dermatan sulfate or pharmacologically acceptable salts thereof having an intrinsic viscosity of about 0.8–2.0 (100 ml/g) as determined with an Ubbelohde viscometer using 0.2M sodium chloride solution as a solvent and at a temperature of about 30°±0.1° C.; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparin sulfate content of about 0.05% or less as determined by inhibitory activity of active factor II in the presence of antithrombin III using bovine intestine derived heparin as a standard substance.

2. The dermatan sulfate or pharmacologically acceptable salts thereof according to claim 1 which are derived from chicken crest.

3. Dermatan sulfate or pharmacologically acceptable salts thereof having between about 2% and about 7% ΔDi-OS disaccharides as determined by enzymatic degradation and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

4. The dermatan sulfate or pharmacologically acceptable salts thereof according to claim 3 which is derived from chicken crest.

5. Dermatan sulfate or pharmacologically acceptable salts thereof having an average molecular weight of from about 25,000 daltons to about 100,000 daltons as determined by gel filtration and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

6. The dermatan sulfate or pharmacologically acceptable salts thereof according to claim 5 which is derived from chicken crest.

7. Dermatan sulfate or pharmacologically acceptable salts thereof having an intrinsic viscosity of about 0.8–2.0 (100 ml/g) as determined with an Ubbelohde viscometer using 0.2M sodium chloride solution as a solvent and at a temperature of about 30°±0.1° C.; between about 2% and about 7% ΔDi-OS disaccharides as determined by enzymatic degradation and high performance liquid chromatography; an average molecular weight of from about 25,000 daltons to about 100,000 daltons as determined by gel filtration and high performance liquid chromatography; and a heparin or heparan sulfate content of about 0.15% or less as determined by heparin or heparan degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of 0.05% or less as determined by inhibitory activity of active factor II in the presence of antithrombin III using bovine intestine derived heparin as a standard substance.

8. The dermatan sulfate or pharmacologically acceptable salts thereof according to claim 7 which is derived from chicken crest.

9. A method for prevention or treatment of thrombosis comprising administering to a patient at risk for or afflicted with thrombosis an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at a temperature of about 30°±0.1° C.; and having between about 2% and about 7% or less ΔDi-OS disaccharides as determined by enzymatic degradation and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

10. A method for prevention or treatment of thrombosis comprising administering to a patient at risk for or afflicted with thrombosis an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at a temperature of about 30°±0.1° C.; an average molecular weight of from about 25,000 daltons to about 100,000 daltons as determined by gel filtration and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

11. A method for prevention or treatment of thrombosis comprising administering to a patient at risk for or afflicted with thrombosis an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at 30°±0.1° C.; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

12. The method for prevention or treatment according to claim 9 wherein the administration is to patients at risk for or afflicted with thrombosis due to bleeding tendency caused by decreased platelet count or coagulation factors.

13. The method for prevention or treatment according to claim 10 wherein the administration is to patients at risk for or afflicted with thrombosis due to bleeding tendency caused by decreased platelet count or coagulation factors.

14. The method for prevention or treatment according to claim 11 wherein the administration is to patients at risk for or afflicted with thrombosis due to bleeding tendency caused by decreased platelet count or coagulation factors.

15. A method for prevention or treatment of disseminated intravascular coagulation comprising administering to a patient at risk for or afflicted with disseminated intravascular coagulation an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at a temperature of about 30°±0.1° C., having between about 2% and about 7% ΔDi-OS disaccharide as determined by enzymatic degradation and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance; or a heparin or heparan sulfate content of about 0.05% or less as determined by inhibitory activity of active factor II in the presence of antithrombin III using bovine intestine derived heparin as a standard substance.

16. A method for prevention or treatment of disseminated intravascular coagulation comprising administering to a patient at risk for or afflicted with disseminated intravascular coagulation an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at 30°±0.1° C.; an average molecular weight of from about 25,000 daltons to about 100,000 daltons as determined by gel filtration and high performance liquid chromatography; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance, or a heparin or heparan sulfate content of about 0.05% or less as determined by inhibitory activity of active factor II in the presence of antithrombin III using bovine intestine derived heparin as a standard substance.

17. A method for prevention or treatment of disseminated intravascular coagulation comprising administering to a patient at risk for or afflicted with disseminated intravascular coagulation an effective amount of dermatan sulfate or pharmacologically acceptable salts thereof, having an intrinsic viscosity of about 0.8–2.0 (100 ml/g) as determined with an Ubbelohde viscometer using 0.2M sodium chloride solution as a solvent and at a temperature of about 30°±0.1° C.; and a heparin or heparan sulfate content of about 0.15% or less as determined by heparin or heparan sulfate degradation enzymes and high performance liquid chromatography; a heparin or heparan sulfate content of about 0.07% or less as determined by inhibitory activity of active factor X in the presence of antithrombin III using bovine intestine derived heparin as a standard substance, or a heparin or heparan sulfate content of about 0.05% or less as determined by inhibitory activity of active factor II in the presence of antithrombin III using bovine intestine derived heparin as a standard substance.

18. Medicinal compositions comprising dermatan sulfate or pharmacologically acceptable salts thereof according to claims 1 to 2, 5 or 7, tissue plasminogen activator, and a pharmacologically acceptable adjuvant.

19. A method for treatment of myocardial infarction by administering to a patient afflicted with myocardial infarction an effective amount of dermatan sulfate or pharmacologically acceptable salts thereof according to claims 1, 2, 5 or 7, and tissue plasminogen activator.

* * * * *